United States Patent [19]
Border

[11] Patent Number: 5,935,127
[45] Date of Patent: Aug. 10, 1999

[54] APPARATUS AND METHOD FOR TREATMENT OF A FRACTURE IN A LONG BONE

[75] Inventor: Robert Border, Bourbon, Ind.

[73] Assignee: Biomet, Inc., Warsaw, Ind.

[21] Appl. No.: 08/992,335

[22] Filed: Dec. 17, 1997

[51] Int. Cl.[6] ................................................. A61B 17/56
[52] U.S. Cl. ................................ 606/62; 606/64; 606/69
[58] Field of Search .................................. 606/62, 63, 64, 606/69, 70

[56] References Cited

U.S. PATENT DOCUMENTS

| | | |
|---|---|---|
| 3,531,561 | 9/1970 | Trehu . |
| 3,636,956 | 1/1972 | Schneider . |
| 3,739,773 | 6/1973 | Schmitt et al. . |
| 3,902,497 | 9/1975 | Casey . |
| 3,937,223 | 2/1976 | Roth . |
| 3,960,151 | 6/1976 | Kuhn . |
| 4,186,448 | 2/1980 | Brekke . |
| 4,429,690 | 2/1984 | Angelino-Pievani . |
| 4,523,591 | 6/1985 | Kaplan et al. . |
| 4,781,183 | 11/1988 | Casey et al. . |
| 4,895,572 | 1/1990 | Chernoff ..................................... 606/64 |
| 5,057,110 | 10/1991 | Kranz et al. . |
| 5,112,333 | 5/1992 | Fixel . |
| 5,190,546 | 3/1993 | Jervis ........................................ 606/62 |
| 5,275,601 | 1/1994 | Gogolewski et al. . |
| 5,413,577 | 5/1995 | Pollock . |
| 5,484,438 | 1/1996 | Pennig . |
| 5,562,667 | 10/1996 | Shuler et al. ............................. 606/62 |
| 5,569,250 | 10/1996 | Sarver et al. . |
| 5,603,715 | 2/1997 | Kessler ..................................... 606/62 |
| 5,618,286 | 4/1997 | Brinker . |
| 5,836,949 | 11/1998 | Campbell, Jr. ............................ 606/62 |
| 5,855,579 | 1/1999 | James et al. .............................. 606/62 |

FOREIGN PATENT DOCUMENTS

0491983A1  7/1992  European Pat. Off. .

OTHER PUBLICATIONS

Orthopaedic Equipment Company, Inc., They Thought He Wouldn't Make The Tournament, 1 page, believed to have been published in 1976.
Biomet Inc., UNIFLEX™ Tibial Nail System, 4 pages, 1995, USA.
Biomet Inc., UNIFLEX® Family Nailing System, 16 pages, 1995, USA.
H. McKellop, et al., Development and Clinical Performance of a Reversible Titanium Alloy Femoral Intramedullary Nail, 16 pages, 1991, USA.
Biomwt Inc., UNIFLEX® Hummeral Nail Surgical Technique, 14 pages, 1997, USA.
Biomet Inc., UNIFLEX® Femoral Nail Surgical Technique, 18 pages, 1996, USA.
Biomet Inc., Titanium Femoral Interlocking Nail, 16 pages, 1995, USA.
Biomet Inc., Vector Intertrochanteric Nail, Version One, 16 pages, 1995, USA.
Biomet Inc., Vector Intertrochanteric Nail, Version Two, 18 pages, 1995, USA.
Biomet Inc., Biomet Retrograde Femoral Nail, 6 pages, 1995, USA.
Biomet Inc., Biomet Retrograde Femoral Nail Surgical Technique, 12 pages, 1995 USA.

*Primary Examiner*—Paul J. Hirsch
*Attorney, Agent, or Firm*—Michael B. McNeil

[57] ABSTRACT

A method of treating a fracture in a long bone comprises the initial step of providing an implant that includes one of a bone plate or an intramedullary nail having a length sized to span the fracture. The implant has at least one opening therethrough that is positioned at a location along its length, and has an amount of resorbable material at least partially filling the at least one opening. The implant is positioned at an implantation site spanning the fracture. A first bore is drilled into the long bone and through the resorbable material along a drill axis. A fastener is then inserted into the long bone through the at least one opening.

20 Claims, 3 Drawing Sheets

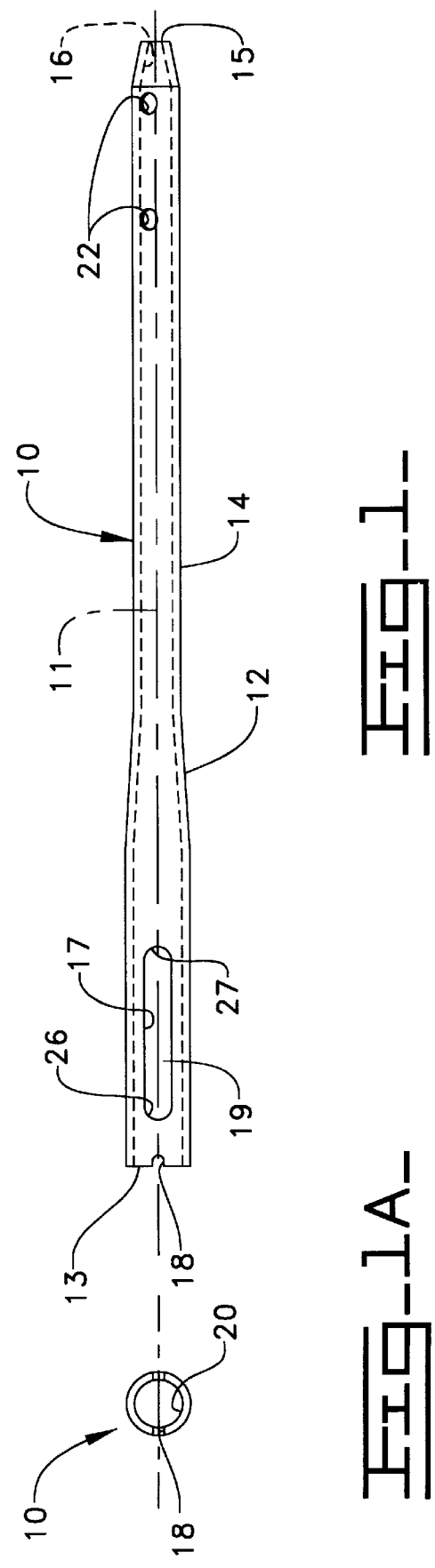

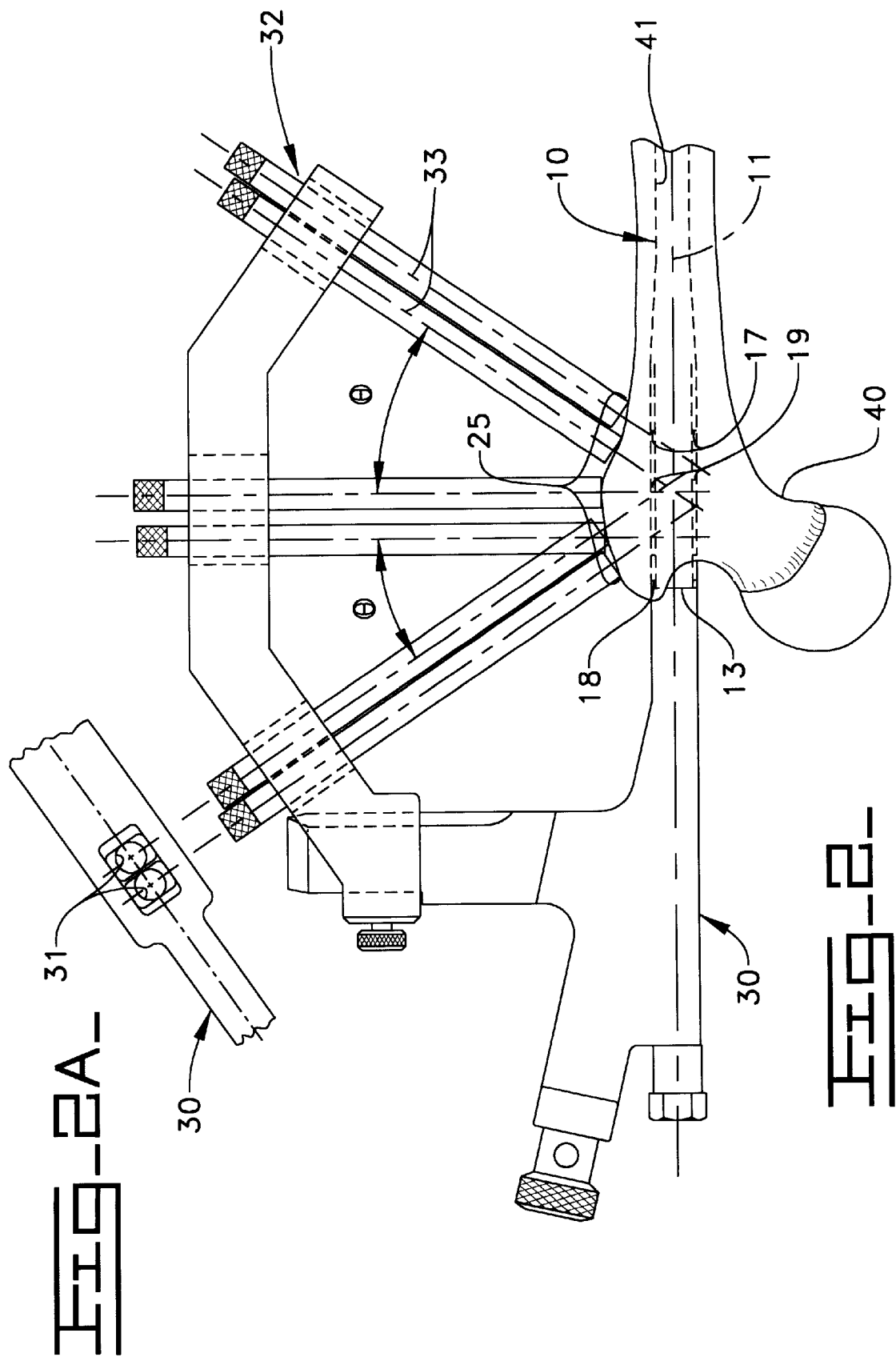

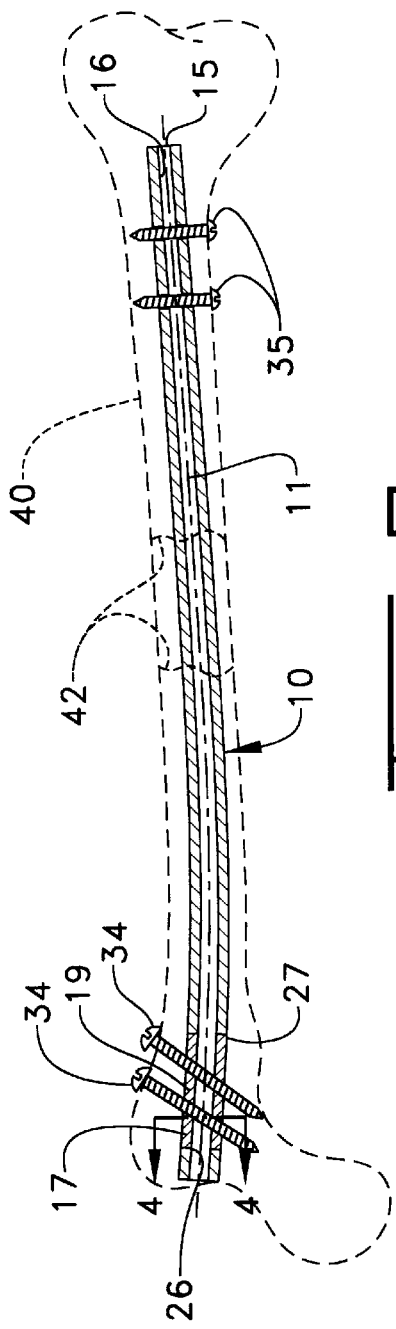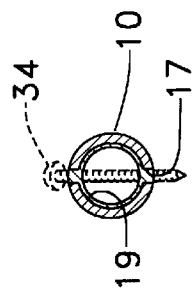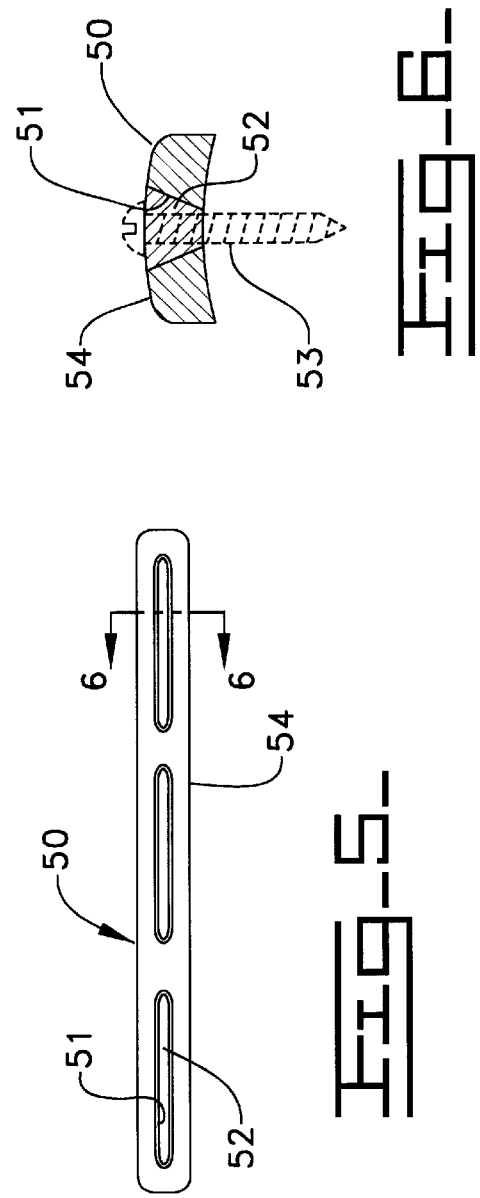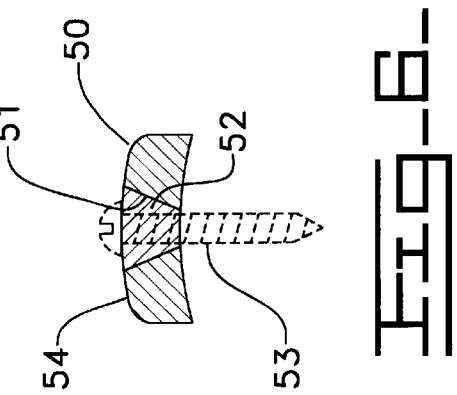

APPARATUS AND METHOD FOR TREATMENT OF A FRACTURE IN A LONG BONE

TECHNICAL FIELD

The present invention relates generally to apparatuses and methods for treatment of fractures in long bones, and more particularly to the treatment of such fractures with an implant that includes a resorbable material.

BACKGROUND ART

It has long been known in the art that fractures in long bones, such as the femur, can be successfully treated through the use of bone plates or intramedullary nails that have lengths many times longer than their widths. The nail or plate is positioned to span the fracture, and attached on opposite ends directly to the bone. While the fracture is healing, the plate or nail prevents twisting and lateral movement in the fracture area, and carries loads across the fracture that the bone is otherwise unable to support. After the fracture has sufficiently healed, the bone plate or intramedullary nail may be detached from the bone and removed from the patient.

In most instances, bone plates and intramedullary nails are made from a suitable surgical grade metallic alloy and are machined with openings that are sized to receive attachment screws at an implantation site. In most instances, these openings do not include threads and have a diameter just larger than the fastening screw. With this arrangement, the fastening screw acts as a pin with respect to the bone plate or intramedullary nail and prevents the same from either rotating or moving laterally with respect to the fractured bone. As a consequence, physicians generally do not have wide latitude in choosing a location through which to drill a fastening bore through a bone. Generally, the fastening bore is drilled perpendicular to the long axis of the bone and through the corresponding opening in the bone plate or intramedullary nail. In general, an improved treatment of the fractured bone can be obtained if the physician has some freedom in choosing the best location on the healthy portion of the bone for attachment of the nail or plate to the bone. In order to gain any freedom in choosing an attachment point with present systems, a physician must often times move the plate or nail to a position that provides less than an optimal support and positioning across the fracture site.

The present invention is directed to overcoming these and other problems associated with the treatment of fractures in long bones.

SUMMARY OF THE INVENTION

In one embodiment, a method of treating a fracture in a long bone comprises the initial step of providing an implant that includes one of a bone plate or an intramedullary nail with a length sized to span the fracture. The implant has at least one opening therethrough that is positioned at a location along its length, and an amount of resorbable material at least partially fills the at least one opening. The implant is positioned at an implantation site spanning the fracture. A first bore is drilled into the long bone and through the resorbable material along a drill axis. A fastener is inserted into the long bone through the at least one opening to attach the implant to the bone.

In another embodiment, an apparatus for treatment of a fracture in a long bone comprises an implant that includes one of either an intramedullary nail or a bone plate having a length sized to span the fracture and at least one opening therethrough that is positioned at a location along the length. An amount of resorbable material is attached to the implant and at least partially fills the at least one opening.

BRIEF DESCRIPTION OF THE DRAWINGS

FIG. 1 is a side view of an intramedullary nail according to one embodiment of the present invention.

FIG. 1a is a left end view of the intramedullary nail of FIG. 1.

FIG. 2 is a side view of an intramedullary nail positioned at an implantation site with a drilling jig attached thereto.

FIG. 2a is a partial top view of a portion of the drilling jig shown in FIG. 2.

FIG. 3 is a sectioned side view of an intramedullary nail according to the present invention attached to a femur at an implantation site.

FIG. 4 is an end sectioned view of the intramedullary nail of FIG. 3 as viewed along section lines 4—4.

FIG. 5 is a top view of a bone plate according to another embodiment of the present invention.

FIG. 6 is a sectioned end view of the bone plate of FIG. 5 as viewed along section lines 6—6.

DETAILED DESCRIPTION OF THE PREFERRED EMBODIMENTS

An intramedullary nail 10 has a long axis 11 and is machined from a suitable metallic alloy into the shape shown with a metallic portion 12. Metallic portion 12 includes a proximal end 13 separated from a distal end 15 by a middle portion 14. A hollow guide bore 16 extends between ends 13 and 15 so that nail 10 can be positioned in a bone with the aid of a conventional guide pin. A slotted shaped opening 17 extends through metallic portion 12 adjacent proximal end 13. In this embodiment, slot 17 has a width just larger than the diameter of an intended fastening screw. Those skilled in the art will appreciate that other suitable fasteners could be substituted for the described screw(s). A pair of notches 18 are machined into proximal end 13 and serve as a means by which one can locate the center of slot 17 when the same is hidden from view in a bone. Slot 17 has a proximal end 26 and a distal end 27. Except for hollow guide bore 16 that passes completely through nail 10, slot 17 is filled with a solid resorbable material 19 that is secured to metallic portion 12 by any suitable means, such as through the use of molding techniques. A portion of guide bore 16 adjacent proximal end 13 is threaded in order to facilitate the attachment of tools during the implantation procedure, such as the drilling jig 30 shown in FIG. 2.

In order to attach the distal portion of nail 10 it includes a pair of fastener bores 22 that are straight with respect to the femoral bone. Notch 18, and hence slot 17, are preferably anteverted left or right about 9° with respect to fastener bores 22. Thus, if nail 10 was used in a left femur, slot 17 would be oriented about plus 9° with respect to fastener bores 22. On the other hand, if the nail is being used in a right femur, slot 17 would be oriented about minus 9° with respect to the fastener bores 22. Although nail 10 is shown in FIG. 1 as not having a bow, those skilled in the art will appreciate that bowed nails could be used to better fit the internal contours of any suitable long bone within which nail 10 is being positioned. Because the physician knows the position and orientation of fastener bores 22 with respect to notch 18 (slot 17), a hole can be drilled into the bone and through the respective fastener bores 22 after nail 10 is positioned at an implantation site spanning a fracture.

Referring now to FIGS. 2–4, in most respects, the implantation procedure used in the present invention is substantially similar to procedures of the prior art. However, because the present invention uses a slot filled with a resorbable material, the physician has a relatively large proximal end fastening area 25 over which to choose the best location to attach the nail 10 to the bone 40. In the preferred embodiment, the nail 10 is advanced along the long axis 11 in the intramedullary canal 41 of bone 40 until it is positioned at an implantation site spanning a fracture 42. A drilling jig 30 is attached to the internal threads 20 of the proximal end of nail 10 and mated to notches 18 as shown in FIG. 2. Because of the size of the slot, and the presence of the absorbable material therein, the physician has a relatively large fastening area 25 over which to choose the best location for drilling and insertion of fastening screws 34.

In this example, nail 10 is designed for attachment at its distal and proximal ends by two separate pairs of attachment screws 35 and 34, respectively. Each pair of screws 34 and 35 are preferably oriented in a parallel relationship, and each pair lies in a plane. Because of the size and shape of slot 17, the physician can choose an entry location in this example plus or minus an angle theta (in this case approximately 35°) with respect to a line perpendicular to long axis 11. After examining the exterior of bone 40, the drilling jig bores 31 are fixed in a desired orientation. Next, the physician drills along fastener axes 33, which in this case are in an angled position 32 approximately 35° off of the line perpendicular to central long axis 11. In other words, the physician then drills into the bone 40 and through slot 17 using drilling jig 30. The drilling jig is then removed and proximal fasteners 34 are passed or threaded into the bone through slot 17. Distal fasteners 35 are positioned, located and drilled in a conventional manner.

Because the resorbable material is capable of being drilled at the implantation site, nail 10 can be positioned at its desired implantation site before the drilling and fastening procedures are performed. One need not be concerned with drilling through the resorbable material at the implantation site because fragments of that material produced during a drilling procedure can be left in the patient and allowed to be resorbed in due course. Because the resorbable material is positioned between the fastener and the metallic portion of the nail, the loads carried by the fastener and the metallic portion of the nail are slowly decreased as the resorbable material is absorbed by the patient's body. The resorbable material provides initial restraint against movement of the implant relative to the fastener, but allows for dynamization of the fracture as the resorbable material decays. Preferably, proximal fasteners 34 are located closer to the distal end 27 than the proximal end 26 of slot 17 in order to allow for better dynamization as the resorbable material begins to resorb. (See FIG. 3).

By controlling, through a particular compound, the rate at which the resorbable material is absorbed, one can control the rate at which loads carried by the nail are resumed by the bone as the fracture heals. To contrast, in prior art devices the load carried by the nail continues to be carried by the same until such time as the fasteners are removed. In some instances, it may be desirable to include an antibiotic compound in the resorbable material in order to inhibit the formation of infections in the long bone being treated.

Although the present invention was initially illustrated for use with an intramedullary nail, the present invention also finds potential application in bone plates, which are also used in treating fractures of long bones. Referring now to FIGS. 5 and 6, a bone plate 50 includes a plurality of relatively large longitudinal slots 51 that are machined into a metallic portion 54. Each of the slots is filled with a resorbable material 52 that is attached to metallic portion 54. Like the previous embodiment, loads transferred from the bone to the plate 50 by a fastener 53 are transferred to metallic portion 54 by the resorbable material 52. Like the previous embodiment, the resorbable material can include an antibiotic to inhibit infections, and can have any suitable decay rate in order to control the rate at which loads are transferred back to the bone as a fracture heals. Thus, the decay rate of the resorbable material eventually permits movement of the implant relative to the bone so that dynamization of the fracture occurs.

The use of resorbable materials in the openings 51 of the bone plate 50 gives the physician wide latitude in choosing where to drill into the patient's bone without compromising on the best placement of the bone plate with respect to the fracture. Because the fastener bores can be drilled at the implantation site, alignment may be easier than with prior art devices can be avoided.

The above description is intended for illustrative purposes only, and is not intended to limit the scope of the present invention in any way. For instance, the size and shape of the openings through the metallic portion of the implant can be much larger than the fastener diameters, be located anywhere along the length of the implant, and/or otherwise be varied significantly from the described embodiments without departing from the intended scope of the present invention. Furthermore, the bores through the resorbable material can be made to be smooth or threaded, depending on the particular application. In some cases it may be desirable to only partially fill the opening through the implant with resorbable material. Thus, the present invention can take a variety of different shapes and sizes, as well as be modified significantly from the example embodiments illustrated without departing from the contemplated scope of the invention, which is defined in terms of the claims set forth below.

I claim:

1. A method of treating a fracture in a long bone comprising the steps of:

providing an implant having a length sized to span said fracture, at least one opening therethrough positioned at a location along said length and an amount of resorbable material at least partially filling said at least one opening;

positioning said implant at an implantation site spanning said fracture;

drilling a first bore into said long bone and through said resorbable material along a drill axis; and inserting a fastener into said long bone through said at least one opening.

2. The method of claim 1 wherein said implant is an intramedullary nail.

3. The method of claim 2 wherein said positioning step includes a step of advancing said intramedullary nail inside said long bone.

4. The method of claim 3 wherein said opening is larger than a diameter of said fastener;

said opening defines at least one fastener axis along which said fastener can pass completely through said intramedullary nail; and the method further comprises a step of locating drilling sites where said at least one fastener axis intersects an outer surface of said long bone.

5. The method of claim 4 wherein said at least one fastener axis is a plurality of axes that are at an angle less than about 35° with respect to a line perpendicular to a long axis of said long bone; and said drilling step is accomplished along one of said plurality of axes.

6. The method of claim 5 wherein said opening is a slot; and the method further comprises the steps of:

drilling a second bore into said bone and through said slot at an orientation about parallel to said first bore; and inserting an additional fastener into said long bone through said slot.

7. The method of claim 6 where said bores are drilled closer to a distal end than a proximal end of said slot.

8. An apparatus for treatment of a fracture in a long bone, comprising:

an implant having a length sized to span said fracture, at least one opening therethrough positioned at a location along said length; and an amount of resorbable material attached to said implant and at least partially filling said at least one opening.

9. The apparatus of claim 8 wherein said implant is an intramedullary nail that is hollow along a long axis.

10. The apparatus of claim 9 further comprising a first fastener having an outer diameter; and wherein said opening is larger than said outer diameter; and said opening defines at least one fastener axis along which said fastener can pass completely through said intramedullary nail.

11. The apparatus of claim 10 wherein said at least one fastener axis is a plurality of axes that are at an angle less than about 35° with respect to a line perpendicular to said long axis.

12. The apparatus of claim 11 wherein said plurality of axes lie in a plane.

13. The apparatus of claim 12 wherein said opening is a slot sized to receive a pair of parallel oriented fasteners therethrough.

14. The apparatus of claim 8 wherein said resorbable material includes an antibiotic compound.

15. A method of treating a fracture in a long bone to provide initial stabilization and subsequent dynamization of the fracture, comprising the steps of:

providing an implant having a length sized to span the fracture, at least one opening therethrough positioned at a location along said length, and an amount of resorbable material at least partially filling said at least one opening;

passing a fastener into the bone and through said at least one opening such that said resorbable material provides initial restraint against movement of said implant relative to said fastener; and allowing said resorbable material to resorb such that said implant is permitted to move relative to said fastener, whereby dynamization of the fracture occurs.

16. The method of claim 14 wherein said opening is larger than a diameter of said fastener;

said opening defines at least one fastener axis along which said fastener can pass completely through said implant; and the method further comprises a step of locating drilling sites where said at least one fastener axis is closer to a distal end than a proximal end of said at least one opening.

17. The method of claim 16 wherein said at least one fastener axis is a plurality of axes that are at an angle less than about 35° with respect to a line perpendicular to a long axis of said long bone; and said passing step is accomplished along one of said plurality of axes.

18. The method of claim 17 wherein said opening is a slot; and the method further comprises the steps of:

drilling fastener bores into said bone and through said slot at an orientation about parallel to one another; and passing an additional fastener into said long bone through said slot.

19. The method of claim 18 wherein said implant is an intramedullary nail.

20. The method of claim 18 wherein the implant is a bone plate.

* * * * *